US008602555B2

(12) United States Patent
Backus et al.

(10) Patent No.: US 8,602,555 B2
(45) Date of Patent: Dec. 10, 2013

(54) METHOD AND SYSTEM FOR TREATING BINOCULAR ANOMALIES

(75) Inventors: Benjamin T. Backus, New Rochelle, NY (US); Kenneth J. Ciuffreda, New York, NY (US); Diana Ludlam, New York, NY (US)

(73) Assignee: The Research Foundation of State University of New York, Albany, NY (US)

( * ) Notice: Subject to any disclaimer, the term of this patent is extended or adjusted under 35 U.S.C. 154(b) by 190 days.

(21) Appl. No.: 13/302,486

(22) Filed: Nov. 22, 2011

(65) Prior Publication Data

US 2012/0127426 A1 May 24, 2012

Related U.S. Application Data

(60) Provisional application No. 61/416,156, filed on Nov. 22, 2010.

(51) Int. Cl.
*A61B 3/00* (2006.01)

(52) U.S. Cl.
USPC .......................................... 351/203; 351/246

(58) Field of Classification Search
USPC .................................................. 351/200–246
See application file for complete search history.

(56) References Cited

U.S. PATENT DOCUMENTS

2009/0153796 A1* 6/2009 Rabner ........................ 351/201
2011/0299034 A1* 12/2011 Walsh et al. ................. 351/206

* cited by examiner

*Primary Examiner* — Mohammed Hasan
(74) *Attorney, Agent, or Firm* — Davis Wright Tremaine LLP; Heather M. Colburn

(57) ABSTRACT

A system for treating binocular anomalies. The system includes one or more imaging devices, one or more visual displays, and a computing device. The imaging devices may include right and left imaging devices that capture images of a patient's right and left eyes, respectively. The displays may include right and left displays that provide right and left visual stimulation, respectively. The computing device identifies right and left locations on the right and left retinas, respectively, based at least in part on images of right and left eyes, respectively. The brain fuses images positioned at the right and left locations on the retinas into a single image. The computing device transmits right and left positioning signals to the right and left displays, respectively, that indicate that the right and left visual stimulation, respectively, are to be displayed so they are positioned at the right and left locations, respectively, on the retinas.

23 Claims, 4 Drawing Sheets

METHOD AND SYSTEM FOR TREATING BINOCULAR ANOMALIES

CROSS-REFERENCE TO RELATED APPLICATIONS

This application makes a claim of priority under 35 USC §119(e) to U.S. provisional application Ser. No. 61/416,156, filed Nov. 22, 2010.

BACKGROUND OF THE INVENTION

1. Field of the Invention

The present invention is directed generally to methods and devices for treating conditions, such as strabismus, in which a patient is unable to achieve reliable binocular fixation.

2. Description of the Related Art

The retina is a light-sensitive tissue lining the inner surface of an eye. The retina converts light to nerve impulses that are transmitted by the optic nerve to the visual cortex of the brain. Vision is the result of the brain's interpretation of these nerve impulses.

Binocular disparity refers to small differences in portions of a scene captured by each eye resulting from each eye viewing the same scene from a slightly different position. These differences make stereoscopic or binocular vision possible. Binocular vision (also referred to as stereopsis) incorporates images from two eyes simultaneously. In other words, the two images are fused together into a single stereoscopic image. The slight differences between the two images seen from slightly different positions make it possible to perceive distances between objects in what is commonly referred to as depth perception.

Binocular vision occurs when both eyes operate together without diplopia, suppression, or visual confusion. Diplopia is the perception of two images of a single object. Binocular diplopia refers to double vision in which images of an object are formed on non-corresponding points on the retinas of the eyes. Suppression is the inability to perceive an image or part of an image from one eye when both eyes are open. Visual confusion is the perception of two objects (one imaged by each eye) at the same location.

Strabismus is a disorder in which the eyes do not line up in the same direction during binocular fixation. In other words, the eyes are looking in different directions instead of fixating on (foveating) a single point. Strabismus can result in double vision (diplopia), visual confusion, uncoordinated eye movements, vision loss in one eye, and a loss of the ability to see in three dimensions also known as a loss of depth perception. Children with strabismus may learn to ignore visual input from one eye (referred to as suppression). If this continues long enough, the eye that the brain ignores may experience a loss of vision referred as amblyopia. Amblyopia is sometimes referred to as "lazy eye."

Orthoptics is the evaluation and nonsurgical treatment of visual disorders caused by improper coordination of the eye muscles, such as strabismus. Binocular vision therapy is another term that can be used as synonymous with orthoptics. Orthoptic devices have been developed to treat strabismus and amblyopia. For example, a prism may be used to bend light to produce a properly aligned image on the retinas of the eyes that the brain could fuse into a stereoscopic image. Similarly, an amblyoscope is an instrument (a reflecting stereoscope) configured to stimulate vision in an amblyopic or lazy eye. An amblyoscope may also be used to measure or train binocular vision. A synoptophore is a type of amblyoscope. A haploscope presents one image to one eye and another image to the other eye and may be used to treat strabismus and amblyopia.

As a practical matter, the terms haploscopes, amblyoscopes, and synoptophores are largely synonymous with one another. There are two primary methods used clinically with these devices. First, the devices are used to provide temporal co-stimulation of a large-field (about 15 degrees of the visual field in diameter). Second, the devices are used to attempt or achieve perceptual fusion of dichoptic displays (displays that are different in each of the two eyes). An example of a dichoptic display is a pair of images, one of a deer and the other of spots. The deer display is shown to one eye and the spots display to the other eye. The brain creates a fused image of a deer with spots on it.

Unfortunately, these conventional approaches provide diffuse and spatially uncertain stimulation to a patient's eyes. Therefore, a need exists for a device configured to provide more precise and/or spatially certain visual stimulation to a patient's eyes. Further, a need exists for other methods and devices for treating strabismus and/or other conditions in which a patient is unable to achieve reliable binocular fixation and thus may not have sufficiently reliable binocular vision. The present application provides these and other advantages as will be apparent from the following detailed description and accompanying figures.

BRIEF DESCRIPTION OF THE SEVERAL VIEWS OF THE DRAWING(S)

DETAILED DESCRIPTION OF THE INVENTION

Figure 1:
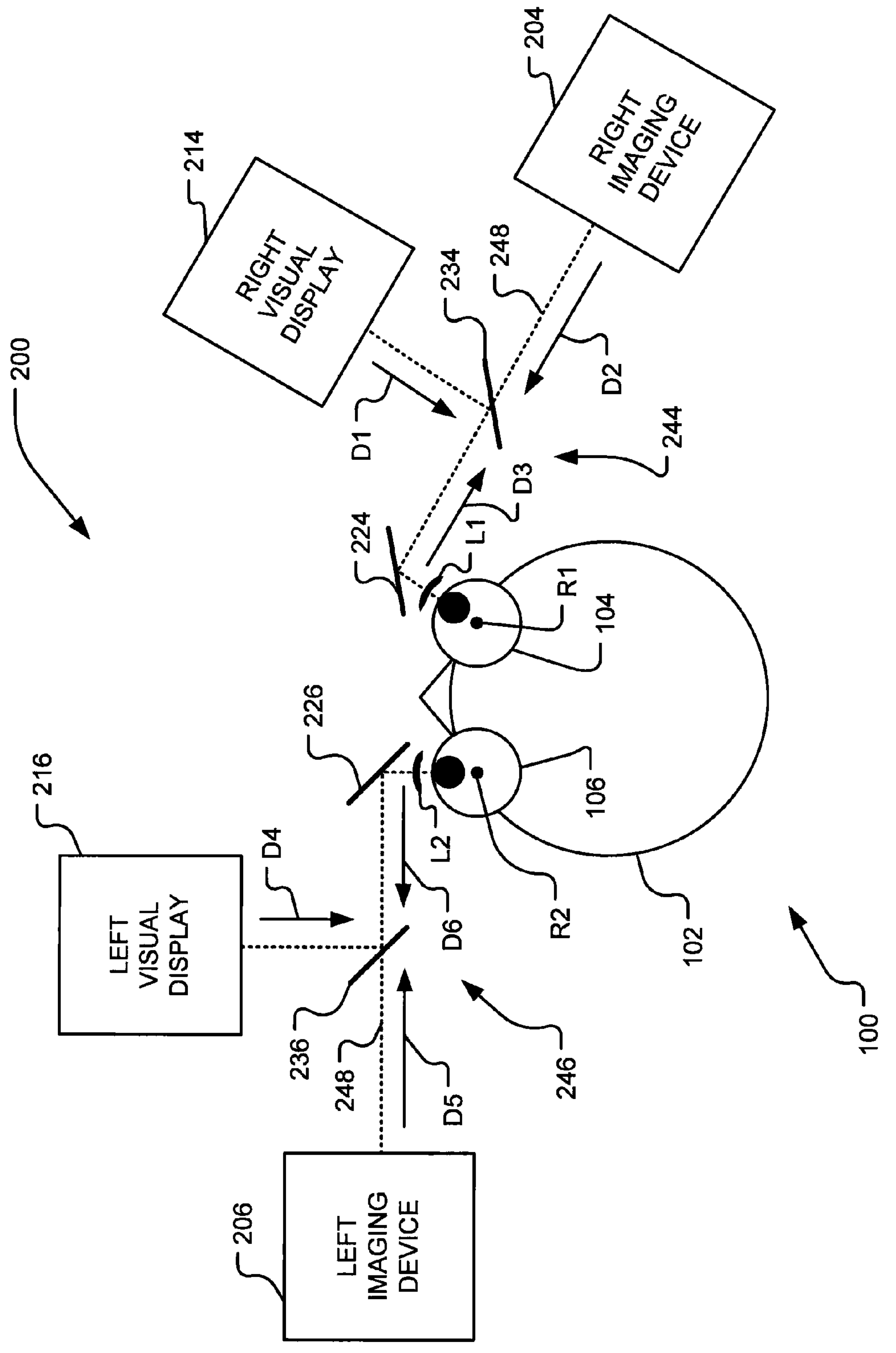
FIG. 1 is a top view of an exemplary embodiment of a device for treating a patient who is unable to achieve reliable binocular fixation.

FIG. 1 illustrates a patient 100 having a head 102 with a right eye 104, and a left eye 106. In the example provided in FIG. 1, the patient's right eye 104 is turned outwardly (toward the right) when the left eye 106 is looking straight ahead. Thus, the patient 100 illustrated has exotropia (an eye that deviates outwardly) and is unable to achieve reliable binocular fixation.

Figure 2:
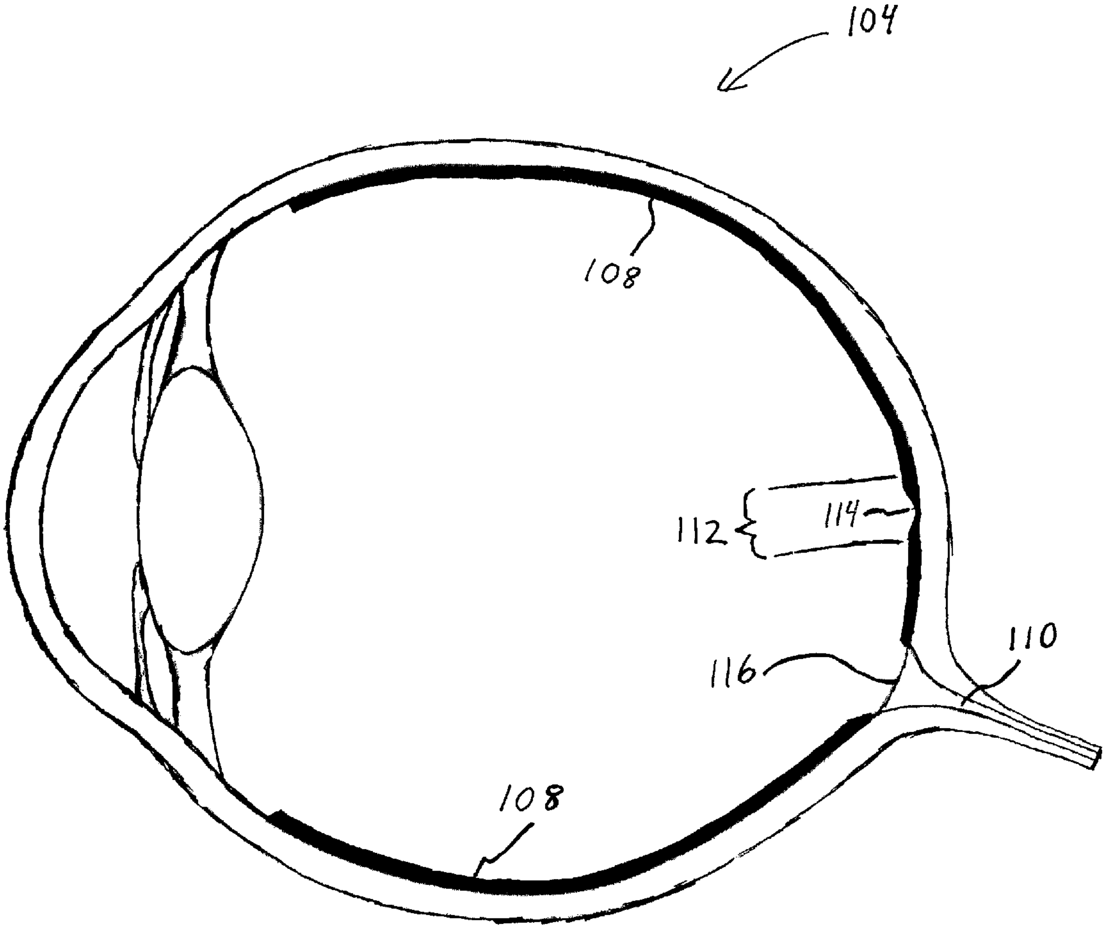
FIG. 2 is an illustration of internal structures of a human eye.

FIG. 2 illustrates some of the internal structures of the right eye 104. The left eye 106 has substantially identical structures to those of the right eye 104. Therefore, for ease of illustration, only the internal structures of the right eye 104 have been illustrated. As is apparent to those of ordinary skill in the art, the right eye includes a retina 108 connected to an optic nerve 110. The retina 108 includes landmarks, such as the macula 112, the fovea 114 (or most central part of the macula), the optic nerve head 116, a specific pattern of blood vessels (not shown), and the like, that may be visible or detectable using retinal imaging technology (e.g., scanning laser ophthalmoscopy ("SLO")). The optic nerve head 116 is the location of the physiological blind spot (punctum caecum) whereat vision is not perceived because the retina 108 does not sense light at that location.

FIG. 1 illustrates a device 200 that includes a right imaging device 204 configured to image the retina 108 (see FIG. 2) of the right eye 104 and a left imaging device 206 configured to image the retina 108 (see FIG. 2) of the left eye 106. In particular embodiments, the right and left imaging devices 204 and 206 are configured to produce and/or capture images of the retinas 108 (see FIG. 2) of the right and left eyes 104 and 106, respectively, in real-time. Optionally, the right and left imaging devices 204 and 206 each include an autofocus mechanism (not shown). The autofocus mechanism may be used by the right and left imaging devices 204 and 206 to collect images of the retinas 108 (see FIG. 2) of the right and left eyes 104 and 106, respectively.

The images produced (or captured) by the right and left imaging devices 204 and 206 are used to detect landmarks on the right and left eyes 104 and 106, respectively. It is believed that the best technology for detecting landmarks on the retinas 108 (see FIG. 2) in real time may be an adaptive optics technology, such as explained in Liang, J., Williams, D. R., and Miller, D. T., Supernormal Vision and High-Resolution Retinal Imaging through Adaptive Optics, Journal of the Optical Society of America A, Optical Society of America, Vol. 14, 2884-2892 (1997), which is incorporated herein by reference in its entirety. However, less expensive and/or more robust technologies also exist, including scanning laser ophthalmoscopy ("SLO") and video retinoscopy. While some of these technologies (e.g., SLO) may not be as precise as adaptive optics technologies, such less expensive and/or more robust technologies may nonetheless be used to detect a landmark on the retina 108 (see FIG. 2) of the right eye 104 and a landmark on the retina 108 (see FIG. 2) of the left eye 106. In particular, these technologies are capable of localizing a center of an extended landmark with high precision because, unlike resolving fine details within the image (e.g. seeing small capillaries that are close together as separate objects), localizing the center of an extended (larger) landmark (such as fovea, optic nerve, large blood vessels, and the like) does not require high resolution.

As is apparent to those of ordinary skill in the art, SLO uses confocal laser scanning microscopy to image the retina 108 (see FIG. 2). SLO provides an adequate spatial resolution for detecting the position of a landmark on the retina 108. SLO further provides a suitable temporal sampling rate for detecting and compensating for small eye movements. In other words, SLO may be used to locate and/or track a particular landmark on the retina 108.

Instead of SLO, a high speed video camera may be used to detect and track a predetermined location (e.g., the location of the blind spot) of the right eye 104 and/or the left eye 106 because a high speed video camera may provide adequate spatial resolution and a suitable temporal sampling rate to detect and track the predetermined location within video images of the eye.

The right and left imaging devices 204 and 206 may be implemented using SLO, high-speed video cameras, or other suitable imaging technologies. Thus, the right imaging device 204 may capture a series of images of the retina 108 of the right eye 104 and the left imaging device 206 may capture a series of images of the retina 108 of the left eye 106. These images may be analyzed (e.g., in real time) to track the positions of landmarks on the retinas 108 (see FIG. 2) of the right and left eyes 104 and 106.

The device 200 uses the right imaging device 204 to track the location of a right landmark of the retina 108 of the right eye 104 and the left imaging device 206 to track the location of a left landmark of the retina 108 of the left eye 106. Thus, using imaging technology, the device 200 may determine the orientations of the right and left eyes 104 and 106 for the purposes of providing stimulation to each eye separately that the brain may fuse together into a single image. In this manner, the device 200 allows patients (such as the patient 100) that are unable to achieve reliable binocular fixation to experience binocular vision. The device 200 may also provide visual stimulation to one or more classes of binocular cortical neurons for the purposes of training those neurons to achieve binocular vision.

The device 200 includes a right display 214 configured to produce visual stimulation to be viewed by the right eye 104 and a left display 216 configured to produce visual stimulation to be viewed by the left eye 106. The autofocus mechanisms (not shown) of the right and left imaging devices 204 and 206 may be used by the device 200 to help ensure that the right and left displays 214 and 216 deliver a well-focused image to the retinas 108 of the right and left eyes 104 and 106, respectively, independent of the accommodative state of the patient 100.

The visual stimulation produced by each of the right and left displays 214 and 216 may include a specific or predetermined pattern, such as a Gabor pattern, or a series of patterns. Each of the right and left displays 214 and 216 may be implemented as a computer-generated display, such as a conventional computer monitor. The right and left displays 214 and 216 may be configured to display high-speed video camera images of real scenes. Alternatively, the right and left displays 214 and 216 may be implemented as physical displays such as real scenes, photographs, or printed images. The right and left displays 214 and 216 may produce still and/or moving images.

Generally speaking, each location on the retina 108 (see FIG. 2) of the right eye 104 corresponds to a location on the retina 108 of the left eye 106. Thus, a pair of corresponding locations on the retinas 108 (see FIG. 2) of the right and left eyes 104 and 106 includes a location on the retina of the right eye that corresponds to a location on the retina of the left eye. Visual stimuli provided to the retina 108 of the right eye 104 at a first location and visual stimuli provided to the retina 108 of the left eye 106 at a location corresponding to the first location (on the retina 108 of the right eye 104) may be fused by brain to construct binocular vision.

A pair of corresponding locations may be points on the retinas 108 of the right and left eyes 104 and 106 having a known physical (i.e. physiological or anatomical) correspondence with one another (whether at zero or nonzero retinal disparity). Correlated retinal locations may be identified using a psychophysical procedure, such as minimization of apparent motion between successively presented dichoptic lights, which is explained in Nakayama K., Human Depth Perception, Society of Photo-Optical Instrumentation Engineers Journal, Society of Photo-Optical Instrumentation Engineers, Vol. 120, 2-9 (1977), which is incorporated herein by reference in its entirety. Alternatively, the corresponding locations on the retinas 108 of the right and left eyes 104 and 106 may be determined using normative data for the empirical horopter. In general, empirically measured corresponding points are not coincident with geometrically corresponding points. Nevertheless, retinal landmarks may be used to identify the corresponding locations using normative data, such as the data described in Schreiber, K. M., Hillis, J. M., Filippini, H. R., Schor, C. M., and Banks, M. S., The Surface of the Empirical Horopter, Journal of Vision, Association for Research in Vision and Ophthalmology, Vol. 8(3):7, 1-20

(2008), which is incorporated herein by reference in its entirety. Referring to FIG. 2, by way of a non-limiting example, the location of the optic nerve head 116 of the retina 108 of the right eye 104 and the location of the optic nerve head 116 of the retina 108 of the left eye 106 (see FIG. 1) may be corresponding locations. By way of another non-limiting example, the location of the fovea 114 of the retina 108 of the right eye 104 and the location of the fovea 114 of the retina 108 of the left eye 106 (see FIG. 1) may be corresponding locations. Further, corresponding locations may be identified relative to landmarks (e.g., the fovea 114, the optic nerve head 116, and the like) on the retinas 108 of the right and left eyes 104 and 106. A specific pattern of blood vessels may also be used as a retinal landmark to identify the same location on the retina 108 of the right eye 104 or the retina 108 of the left eye 106 over time. For example, a specific pattern of blood vessels may be used to stimulate the same area of peripheral retina on several different days.

Typically, binocular cortical neurons (not shown) respond best to stimuli placed at corresponding locations on the two retinas 108 (or, more specifically, to stimuli placed near an "empirical horopter"). Many neurons prefer a pattern including a "Gabor" pattern with a specific temporal frequency, spatial frequency, size, orientation, and binocular disparity. Some neurons respond well to more complicated patterns such as collections of dots. The right and left displays 214 and 216 are each configured to produce the aforementioned patterns to which at least a portion of the binocular cortical neurons respond. The right and left displays 214 and 216 may also be configured to produce other visual stimuli that provide binocular cortical neurons with the types of inputs that help them develop toward perceiving binocular vision. It is believed that delivering such patterns to corresponding locations on the retinas 108 of the right and left eyes 104 and 106 of the patient 100 may provide a basis for building or improving binocular vision in the patient 100 (e.g., a child or an adult).

The right and left displays 214 and 216 are each configured to produce high contrast visual stimuli at specific spatial frequencies, orientations, and disparities. For example, Gabor stimuli may use a carrier spatial frequency within a range of about 0.1 cycles per degree to about 60 cycles per degree, corresponding to the range of the human contrast sensitivity function, which has its peak sensitivity at approximately 3-5 cycles per degree in the normal human visual system. These patterns may be displayed at any or all orientations within a range 0 degrees to 180 degrees, and may be presented with a binocular disparity in the horizontal or vertical direction of zero (in other words, on the horopter) or within the range of normal human vision (typically not more than 10 degrees of disparity).

The envelope of the Gabor stimulus may be large enough to contain a few cycles of the carrier. The right and left displays 214 and 216 may produce a series of different visual stimuli that is correlated in both space and time such that the brain may fuse the visual stimuli provided to the right and left eyes 104 and 106 into a single stereoscopic image. The fused image may be static, moving, or a combination thereof.

Different visual stimuli may target one or more different classes of binocular cortical neurons. In particular, the right and left displays 214 and 216 may produce one or more patterns (e.g., dots, lines, simple shapes, Gabor patterns, drifting Gabor patterns, more complex patterns, patterns of randomly spaced dots, images of simple objects, images of scenes, combinations thereof, and the like) for each class of binocular cortical neurons. These patterns may be displayed serially in a sweeping fashion to serially target different classes of binocular cortical neurons. Binocular cortical neurons that may be targeted exist in human brain areas V1, V2, V3, LO-1, LO-2, V3A, hV4, and MT+.

The visual stimulus produced by the right and left displays 214 and 216 may be matched to the known receptive fields of binocular neurons in human visual cortex, which may require precise positioning of the stimuli on the retinas 108 (see FIG. 2) of the right and left eyes 104 and 106. As explained above, the right and left imaging devices 204 and 206 may determine the orientation of the right and left eyes 104 and 106, respectively. This orientation information may be used to position visual stimuli on the retinas 108 (see FIG. 2) of the right and left eyes 104 and 106 at corresponding locations. In other words, the orientation information may be used to position the right and left displays 214 and 216 (or the stimulation produced thereby) such that the brain may fuse the images captured by each of the retinas 108 into a single (still or moving) stereoscopic image. Further, the right and left imaging devices 204 and 206 may be used to verify that the visual simulation produced by the right and left displays 214 and 216, respectively, is positioned on corresponding locations of the retinas 108 of the right and left eyes 104 and 106, respectively.

In the embodiment illustrated, the device 200 includes a right mirror 224 positioned adjacent to the right eye 104 of the patient 100. The right display 214 produces visual stimulation (not shown) that is reflected by the right mirror 224 onto the retina 108 (see FIG. 2) of the right eye 104. At the same time, the right imaging device 204 may produce a scanning signal (e.g., a laser beam) that is reflected by the right mirror 224 onto the retina 108 of the right eye 104. A reflected scanning signal (reflected by the retina 108 of the right eye 104) exits the right eye 104 and is reflected by the right mirror 224 back toward the right imaging device 204. The reflected scanning signal is used to detect the location of a landmark on the retina 108 of the right eye 104.

Optionally, an ophthalmic lens "L1" may be interpositioned in the optical path between the right eye 104 and the right mirror 224. The lens "L1" may be configured to allow a patient with a refractive error to see the visual stimulus displayed by the right visual display 214 clearly without wearing contact lenses.

Alternatively, the lens "L1" may be configured to aid with experiments, collecting measurements, and the like.

The device includes a left mirror 226 positioned adjacent to the left eye 106 of the patient 100. The left display 216 produces visual stimulation (not shown) that is reflected by the left mirror 226 onto the retina 108 of the left eye 106. At the same time, the left imaging device 206 may produce a scanning signal (e.g., a laser beam) that is reflected by the left mirror 226 onto the retina 108 of the left eye 106. Similarly, a reflected scanning signal (reflected by the retina 108 of the left eye 106) exits the left eye 106 and is reflected by the left mirror 226 back toward the left imaging device 206. The reflected scanning signal is used to detect the location of a landmark on the retina 108 of the left eye 106.

Optionally, an ophthalmic lens "L2" may be interpositioned in the optical path between the left eye 106 and the left mirror 226. The lens "L2" may be configured to allow a patient with a refractive error to see the visual stimulus displayed by the left visual display 216 clearly without wearing contact lenses. Alternatively, the lens "L2" may be configured to aid with experiments, collecting measurements, and the like.

A half-silvered right mirror 234 is positioned to allow the scanning signal produced by the right imaging device 204 to pass therethrough. The half-silvered right mirror 234 is also positioned to reflect the visual stimulation produced by the right display 214 such that the visual stimulation is reflected by the right mirror 224 onto the retina 108 of the right eye 104. In the embodiment illustrated, the visual stimulation produced by the right display 214 travels along a direction (indicated by arrow "D1") toward the half-silvered right mirror 234 that is substantially orthogonal to a direction (indicated by arrow "D2") in which the scanning signal travels from the right imaging device 204 through the half-silvered right mirror 234 and toward the right mirror 224. The reflected scanning signal travels from the right mirror 224 through the half-silvered right mirror 234 and toward the right imaging device 204 in a direction (indicated by arrow "D3") that is substantially opposite the direction indicated by arrow "D2." Each of the right mirror 224 and the half-silvered right mirror 234 may be oriented at approximately a 45 angle relative to the directions indicated by arrows "D2" and "D3." After being reflected by the half-silvered right mirror 234, the visual stimulation produced by the right display 214 travels along the direction indicated by arrow "D2" toward the right mirror 224.

A half-silvered left mirror 236 is positioned to allow the scanning signal produced by the left imaging device 206 to pass therethrough. The half-silvered left mirror 236 is also positioned to reflect the visual stimulation produced by the left display 216 such that the visual stimulation is reflected by the left mirror 226 onto the retina 108 of the left eye 106. In the embodiment illustrated, the visual stimulation produced by the left display 216 travels along a direction (indicated by arrow "D4") toward the half-silvered left mirror 236 that is substantially orthogonal to a direction (indicated by arrow "D5") in which the scanning signal travels from the left imaging device 206 through the half-silvered left mirror 236 and toward the left mirror 226. The reflected scanning signal travels from the left mirror 226 through the half-silvered left mirror 236 and toward the left imaging device 206 in a direction (indicated by arrow "D6") that is substantially opposite the direction indicated by arrow "D5." Each of the left mirror 226 and the half-silvered left mirror 236 may be oriented at approximately a 45 angle relative to the directions indicated by arrows "D5" and "D6." After being reflected by the half-silvered left mirror 236, the visual stimulation produced by the left display 216 travels along the direction indicated by arrow "D5" toward the left mirror 226.

As mentioned above, the visual stimulation produced by the right and left displays 214 and 216 is positioned on the retinas 108 (see FIG. 2) of the right and left eyes 104 and 106, respectively, at corresponding locations so that the patient's brain can fuse the visual stimulation into a single stereoscopic image. Such visual stimulation may also train binocular cortical neurons such they are able to build binocular vision in children and adults. The device 200 includes positionable right and left arm assemblies 244 and 246 configured to be adjustable to position the visual simulation produced by the right and left displays 214 and 216, respectively, onto the corresponding locations of the retinas 108 of the right and left eyes 104 and 106, respectively.

The right and left arm assemblies 244 and 246 may each include a rigid arm 248. In the embodiment illustrated, the right display 214, the right imaging device 204, the right mirror 224, and the half-silvered right mirror 234 are mounted on the arm 248 of the right arm assembly 244 and are positionable thereby relative to the right eye 104. The left display 216, the left imaging device 206, the left mirror 226, and the half-silvered left mirror 236 are mounted on the arm 248 of the left arm assembly 246 and are positionable thereby relative to the left eye 106. The arms 248 of the right and left arm assemblies 244 and 246 are positionable independently of one another.

The arm 248 of the right arm assembly 244 may be rotatable or otherwise positionable about the patient's head 102 relative to a right center of rotation "R1" substantially collocated with a center of the right eye 104. The arm 248 of the right arm assembly 244 is rotatable or otherwise positionable about the right center of rotation "R1" vertically as well as horizontally. Thus, the right arm assembly 244 is positionable at locations along a surface of a sphere (not shown) centered at the right center of rotation "R1" having a diameter selected to provide a suitable range of rotation about the right center of rotation. This range of rotation can be accomplished by, but is not limited to, a mechanical arrangement whereby a vertical axle (not shown) is placed under the chin of the patient 100 such that the axis of rotation contains the center of rotation "R1," in order to achieve a desired azimuth. To achieve a desired elevation, a slider (not shown) may be positioned on a circular track (not shown) that is positioned within a vertical plane, with the track lying along an annulus that is centered on the center of rotation "R1." Alternatively, the position of the arm may be controlled along six degrees of freedom (x, y, z, pitch, roll, and yaw) using a computer-controlled robotic positioning device (not shown).

Similarly, the arm 248 of the left arm assembly 246 may be rotatable or otherwise positionable about the patient's head 102 relative to a left center of rotation "R2" substantially collocated with a center of the left eye 106. The arm 248 of the left arm assembly 246 is rotatable or otherwise positionable about the left center of rotation "R2" vertically as well as horizontally. Thus, the left arm assembly 246 is positionable at locations along a surface of a sphere (not shown) centered at the left center of rotation "R2" having a diameter selected to provide a suitable range of rotation about the left center of rotation.

Components mounted to the arm 248 of the right arm assembly 244 (i.e., the right display 214, the right imaging device 204, the right mirror 224, and the half-silvered right mirror 234) are rotatable or otherwise positionable as a unit at an appropriate location relative to the right eye 104 (which will not necessarily be pointed in a convenient direction). Similarly, components mounted to the arm 248 of the left arm assembly 246 (i.e., the left display 216, the left imaging device 206, the left mirror 226, and the half-silvered left mirror 236) are rotatable or otherwise positionable as a unit at an appropriate location relative to the left eye 106 (which will not necessarily be pointed in a convenient direction).

Large positional adjustments may be effected by rotating or otherwise positioning the arms 248 of the right and left arm assemblies 244 and 246. For example, in FIG. 1, the patient 100 is illustrated looking into the device 200. The arm 248 of the right arm assembly 244 is illustrated after having been rotated to compensate for the patient's exotropia in the right eye 104 (which deviates outwardly). Thus, the positioning of the arm 248 of the right arm assembly 244 may be used to compensate for the rotational position of the right eye 104. The visual stimulation produced by the right display 214 is positioned at a first location on the retina 108 of the right eye 104. The arm 248 of the left arm assembly 246 is illustrated in a position that positions the visual stimulation produced by the left display 216 on a location of the retina 108 of the left eye 106 that corresponds to the first location on the retina of the right eye 104.

By way of non-limiting examples, the physical positioning of each of the right and left arm assemblies 244 and 246 relative to the right and left eyes 104 and 106, respectively, may be accomplished by manual control of manual mechanisms (not shown), manual control of motorized mechanisms (not shown), automatic (robotic) positioning mechanisms (not shown) using motorized mechanisms, and the like.

By way of a non-limiting example, a right automatic (robotic) positioning mechanism (not shown) may determine the position of the right arm assembly 244 and a left automatic (robotic) positioning mechanism (not shown) may determine the position of the left arm assembly 246. For ease of illustration, methods of using the right automatic (robotic) positioning mechanism to automatically position the right arm assembly 244 with respect to the right eye 104 will be described in detail. However, as is appreciated by those of ordinary skill in the art, substantially identical methods may be used with respect to the left automatic (robotic) positioning mechanism to automatically position the left arm assembly 246 with respect to the left eye 106. Portions of the right and left automatic (robotic) positioning mechanisms may be implemented using software executing on a computing device (e.g., the computing device 268).

The right automatic (robotic) positioning mechanism (not shown) may use a negative feedback loop to control the distance between components the device 200 mounted to the right arm assembly 244 and the ocular surface of the right eye 104 (for example, a minimum permitted distance between the device 200 and the ocular surface). Alternatively, the right automatic (robotic) positioning mechanism may use a negative feedback loop to control six degrees of freedom (or any equivalent parameterization of space) that describe the position of components the device 200 mounted to the right arm assembly 244 relative to the right eye 104 of the patient 100. By way of a non-limiting example, the six degrees of freedom may include x, y, z, roll, pitch, and yaw. Distance (or 6D position) relative to the right eye 104 may be measured from images of the outside of the right eye 104 captured by a camera (not shown) together with known position and orientation of the camera. The right automatic (robotic) positioning mechanism may also use images of the retina 108 of the right eye 104, and an automatic adjustment rule (such as gradient of ascent on the size of the solid angle subtended by the retina), to optimize one or more aspects of retinal image quality, such as size, focus, or retinal location. Several factors may be combined into a single statistic that expresses the quality of the current physical position of each of the right arm assembly 244. This statistic could be minimized or maximized by moving the right arm assembly 244 according to an adaptive rule such as gradient of descent. As mentioned above, the methods described above may be used by (or adapted for use by) the left automatic (robotic) positioning mechanism to automatically position the left arm assembly 246 with respect to the left eye 106.

Figure 3:
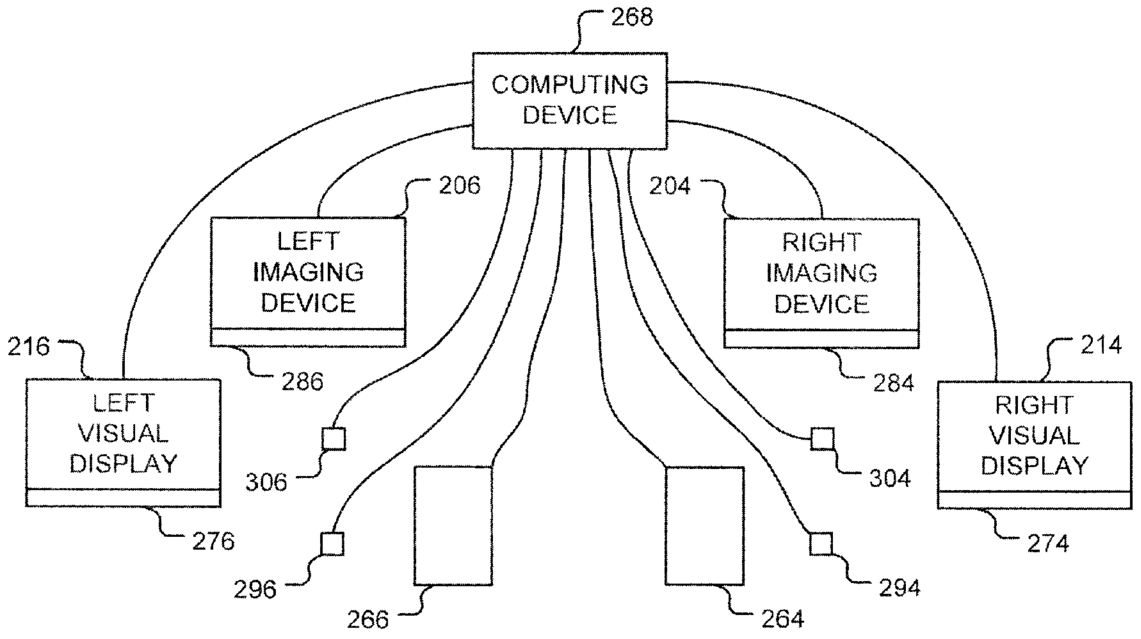
FIG. 3 is a block diagram illustrating electrical components of the device of FIG. 1.

FIG. 3 is a block diagram illustrating electrical components of the device 200. The device 200 may include a right controller 264 operable to control the position of the arm 248 of the right arm assembly 244 relative to the patient 100. As is apparent to those of ordinary skill in the art, the right arm assembly 244 includes positioning components (not shown), such as motors, piezoelectric components, hydraulic cylinders, actuators, and the like, operable to rotate, raise, lower, and otherwise position the arm 248 of the right arm assembly 244 relative to the patient 100. The right controller 264 is connected to a computing device 268. The right controller 264 receives a right positioning signal from the computing device 268 instructing the right controller 264 how to position the arm 248 of the right arm assembly 244 relative to the patient 100. The right controller 264 operates the positioning components (not shown) to position the arm 248 of the right arm assembly 244 in response to receiving these instructions from the computing device 268.

The device 200 may include a left controller 266 operable to control the position of the arm 248 of the left arm assembly 246 relative to the patient 100. As is apparent to those of ordinary skill in the art, the left arm assembly 246 includes positioning components (not shown), such as motors, piezoelectric components, hydraulic cylinders, actuators, and the like, operable to rotate, raise, lower, and otherwise position the arm 248 of the left arm assembly 246 relative to the patient 100. The left controller 266 is connected to the computing device 268 and receives a left positioning signal from the computing device 268 instructing the left controller 266 how to position the arm 248 of the left arm assembly 246 relative to the patient 100. The left controller 266 operates the positioning components to position the arm 248 of the left arm assembly 246 in response to receiving these instructions from the computing device 268.

In alternate embodiments, an operator may manually position the arms 248 of the right and left arm assemblies 244 and 246. In such embodiments, the positioning components (not shown) may be configured to be operated manually to adjust and fix the positions of the arms 248 of the right and left arm assemblies 244 and 246.

The computing device 268 is connected to the right imaging device 204 and receives a right imaging signal therefrom. As discussed above, the right imaging device 204 receives the right reflected scanning signal (reflected by the retina 108 of the right eye 104). The right imaging device 204 is operable to produce the right imaging signal based on the right reflected scanning signal. The computing device 268 is operable to analyze the right imaging signal to identify the position of a landmark on the retina 108 of the right eye 104 and generate the right positioning signal, which is configured to position the visual stimulus of the right display 214 on a first position on the retina 108 of the right eye 104 relative to the landmark identified.

The computing device 268 is also connected to the left imaging device 206 and receives a left imaging signal therefrom. As discussed above, the left imaging device 206 receives the left reflected scanning signal (reflected by the retina 108 of the left eye 106). The left imaging device 206 is operable to produce the left imaging signal based on the left reflected scanning signal. The computing device 268 is operable to analyze the left imaging signal to identify the position of a landmark on the retina 108 of the left eye 106 and generate the left positioning signal, which is configured to position the visual stimulus provided by the left display 216 on a second position on the retina 108 of the left eye 106 relative to the landmark identified that corresponds with the first position on the retina 108 of the right eye 104.

The computing device 268 may be configured to analyze the right and left imaging signals in real-time and generate the right and left positioning signals to adjust the positioning of the visual stimulus provided by the right and left displays 214 and 216, as necessary, to maintain the visual stimulus on corresponding locations on the retinas 108 of the right and left eyes 104 and 106, respectively.

The computing device 268 may be connected to each of the right and left displays 214 and 216. The computing device 268 may provide a right stimulus signal to the right display 214 and a left stimulus signal to the left display 216. The right and left stimulus signals are delivered at the same time and cause the right and left displays 214 and 216 to provide temporally aligned (or synchronized) visual stimulation to the patient 100. Optionally, the right display 214 and/or the left display 216 may be configured to adjust the position of the visual stimuli displayed thereby. Such adjustments may be used to position the visual stimulation at corresponding locations on the retinas 108 of the right and left eyes 104 and 106. Further, the computing device 268 may instruct the right display 214 and/or the left display 216 to adjust the position of the visual stimuli displayed thereby.

Small positional adjustments for small amounts of esotropia (eye deviation inward) or exotropia (eye deviation outward), as often seen after eye surgery has been performed, may be effected not only by adjusting the stimulus position within the right visual display 214 and/or the left visual display 216, but also by adjusting the positions of one or more of the components mounted on the arm 248 of the right arm assembly 244 and/or adjusting the positions of one or more of the components mounted to the arm 248 of the left arm assembly 246.

For example, referring to FIG. 3, the position of the right display 214 may be modified using fine adjustment controls 274 provided for the right display. The computing device 268 may be connected to and operable to control or operate the fine adjustment controls 274 to modify the position of the right display 214. Alternatively, an operator may manually operate the fine adjustment controls 274 to modify the position of the right display 214.

The position of the left display 216 may be modified using fine adjustment controls 276 provided for the left display. The computing device 268 may be connected to and operable to control or operate the fine adjustment controls 276 to modify the position of the left display 216. Alternatively, an operator may manually operate the fine adjustment controls 276 to modify the position of the left display 216.

The position of the right imaging device 204 may be modified using fine adjustment controls 284 provided for the right imaging device. The computing device 268 may be connected to and operable to control or operate the fine adjustment controls 284 to modify the position of the right imaging device 204 (see FIG. 1). Alternatively, an operator may manually operate the fine adjustment controls 284 to modify the position of the right imaging device 204.

The position of the left imaging device 206 may be modified using fine adjustment controls 286 provided for the left imaging device. The computing device 268 may be connected to and operable to control or operate the fine adjustment controls 286 to modify the position of the left imaging device 206. Alternatively, an operator may manually operate the fine adjustment controls 286 to modify the position of the left imaging device 206.

Optionally, the positioning of the right mirror 224 (see FIG. 1) may be modified by a right adjustment mechanism 294 (e.g., an actuator) connected to the right mirror and configured to change the position and/or orientation of the right mirror. The computing device 268 may be connected to and operable to control or operate the right adjustment mechanism 294 to modify the position of the right mirror 224 (see FIG. 1). Alternatively, an operator may manually operate the right adjustment mechanism 294 to modify the position of the right mirror 224 (see FIG. 1).

The positioning of the left mirror 226 may be modified by a left adjustment mechanism 296 (e.g., an actuator) connected to the left mirror and configured to change the position and/or orientation of the left mirror. The computing device 268 may be connected to and operable to control or operate the left adjustment mechanism 296 to modify the position of the left mirror 226 (see FIG. 1). Alternatively, an operator may manually operate the left adjustment mechanism 296 to modify the position of the left mirror 226 (see FIG. 1). Making the position and/or orientation of the right and left mirrors 224 and 226 adjustable may allow for a wider range of eye position tracking.

Optionally, the positioning of the half-silvered right mirror 234 (see

FIG. 1) may be modified by a right adjustment mechanism 304 (e.g., an actuator) connected to the half-silvered right mirror and configured to change the position and/or orientation of the half-silvered right mirror. The computing device 268 may be connected to and operable to control or operate the right adjustment mechanism 304 to modify the position of the half-silvered right mirror 234 (see FIG. 1). Alternatively, an operator may manually operate the right adjustment mechanism 304 to modify the position of the half-silvered right mirror 234 (see FIG. 1).

The effect of modifying the position of the half-silvered right mirror 234 is to move the position of the stimulus, as depicted on the right visual display 214, to a new location on the retina 108 of the right eye 104, without substantially moving the image of the retina of the right eye, as detected by the right imaging device 204.

The positioning of the half-silvered left mirror 236 may be modified by a left adjustment mechanism 306 (e.g., an actuator) connected to the half-silvered left mirror and configured to change the position and/or orientation of the half-silvered left mirror. The computing device 268 may be connected to and operable to control or operate the left adjustment mechanism 306 to modify the position of the half-silvered left mirror 236 (see FIG. 1). Alternatively, an operator may manually operate the left adjustment mechanism 306 to modify the position of the half-silvered left mirror 236 (see FIG. 1).

The effect of modifying the position of the half-silvered left mirror 236 is to move the position of the stimulus, as depicted on the left visual display 216, to a new location on the retina 108 of the left eye 106, without substantially moving the image of the retina of the left eye, as detected by the left imaging device 206.

Returning to FIG. 1, the patient 100 is expected to keep the head 102 substantially still. In the embodiment illustrated, the patient's head 102 is not restrained. In alternate embodiments, the patient's head 102 may be restrained. By way of a non-limiting example, the device 200 may be configured to be mounted on the patient's head 102 for movement therewith. In such embodiments, accurate stimulation may be delivered to the patient's right and left eyes 104 and 106 without measuring and/or analyzing head motion. Nevertheless, the device 200 may be configured to compensate for small head movements without measuring and/or analyzing head movement.

Figure 4:
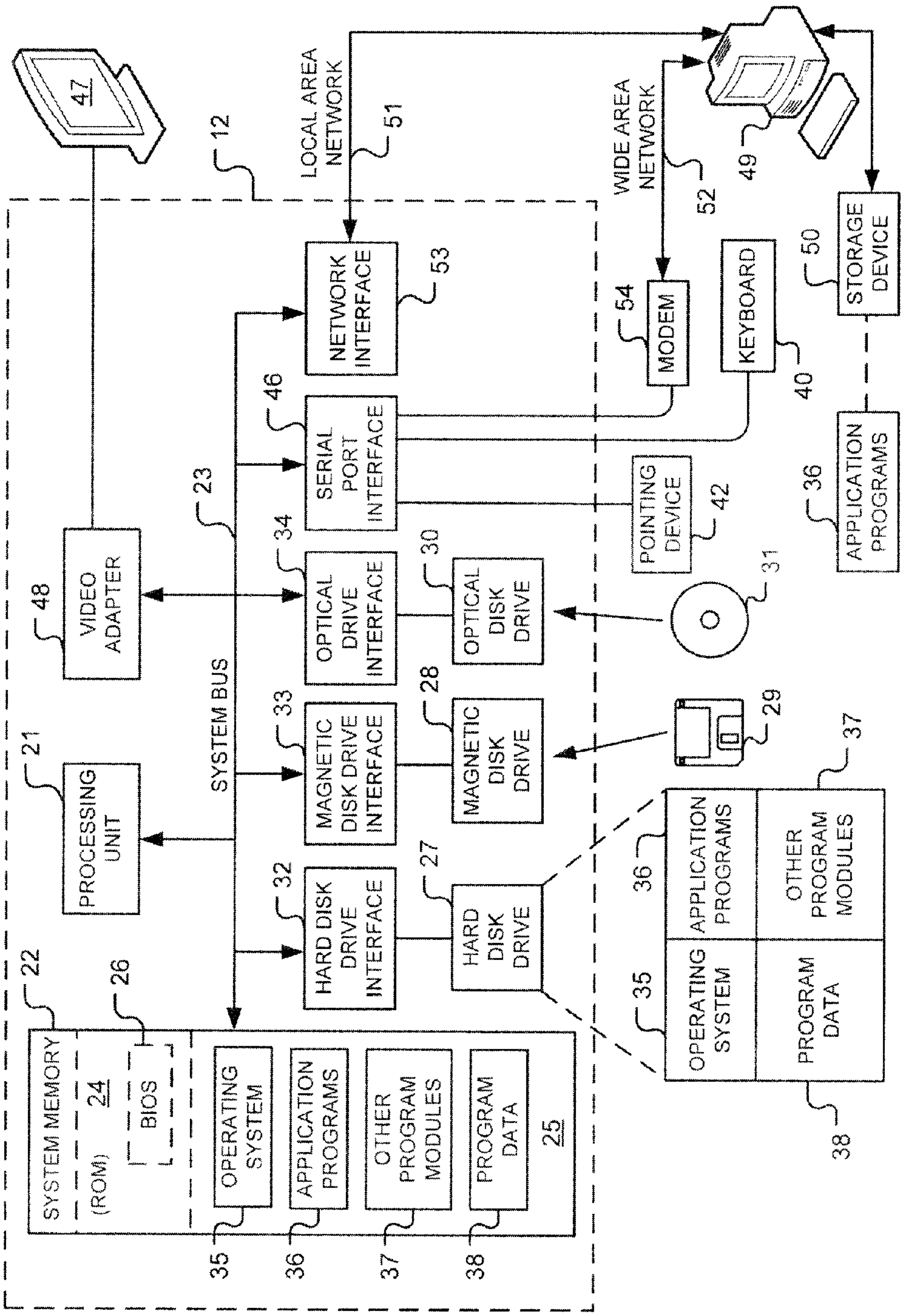
FIG. 4 is a diagram of a hardware environment and an operating environment in which the computing device of FIG. 3 may be implemented.

FIG. 4 is a diagram of hardware and an operating environment in conjunction with which implementations of the computing device 268 may be practiced. The description of FIG. 4 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those skilled in the art will appreciate that implementations may be practiced with other computer system configurations, including hand-held devices, multiprocessor systems, microprocessor-based or programmable consumer electronics, network PCs, minicomputers, mainframe computers, and the like. Implementations may also be practiced in distributed computing environments where tasks are performed by remote processing devices that are linked through a communications network. In a distributed computing environment, program modules may be located in both local and remote memory storage devices.

The exemplary hardware and operating environment of FIG. 4 includes a general-purpose computing device in the form of a computing device 12. The computing device 268 may be implemented using one or more computing devices like the computing device 12.

The computing device 12 includes the system memory 22, a processing unit 21, and a system bus 23 that operatively couples various system components, including the system memory 22, to the processing unit 21. There may be only one or there may be more than one processing unit 21, such that the processor of computing device 12 comprises a single central-processing unit (CPU), or a plurality of processing units, commonly referred to as a parallel processing environment. The computing device 12 may be a conventional computer, a distributed computer, or any other type of computer.

The system bus 23 may be any of several types of bus structures including a memory bus or memory controller, a peripheral bus, and a local bus using any of a variety of bus architectures. The system memory may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those skilled in the art that any type of computer-readable media which can store data that is accessible by a computer, such as magnetic cassettes, flash memory cards, USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, USB drives, and the like) accessible by the processing unit 21 may be considered components of the system memory 22.

Figure 5:
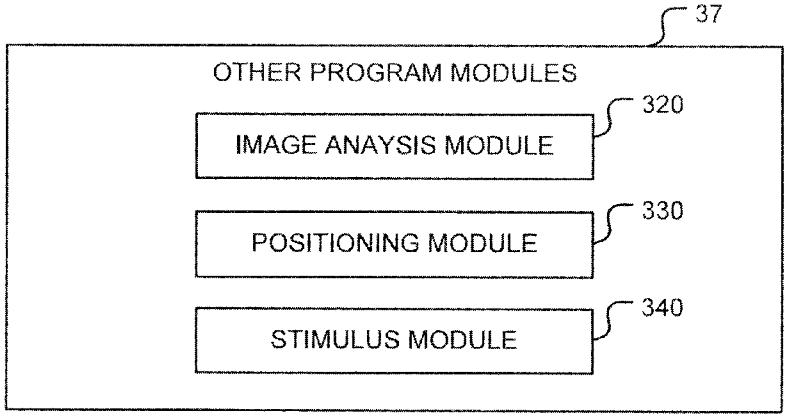
FIG. 5 is block diagram illustrating other programming modules stored in a memory of or accessible by the computing device of FIG. 3.

A number of program modules may be stored on the hard disk drive 27, magnetic disk 29, optical disk 31, ROM 24, or RAM 25, including an operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, or the like. These and other input devices are often connected to the processing unit 21 through a serial port interface 46 that is coupled to the system bus 23, but may be connected by other interfaces, such as a parallel port, game port, or a universal serial bus (USB). A monitor 47 or other type of display device is also connected to the system bus 23 via an interface, such as a video adapter 48. In addition to the monitor, computers typically include other peripheral output devices (not shown), such as speakers and printers. The monitor 47 may be used to display a representation of both retinas simultaneously, along with the pattern of visual stimulation superimposed on those images. The operator may observe, control, or otherwise adjust the location or type of stimulation by viewing these images. Alternatively, the location of stimulation may be controlled by the computing device 268 and programming modules 37 (see FIG. 4), which as illustrated in FIG. 5 and described below, may include an image analysis module 320, a positioning module 330, and a stimulus module 340.

The input devices described above are operable to receive user input and selections. Together the input and display devices may be described as providing a user interface.

The computing device 12 may operate in a networked environment using logical connections to one or more remote computers, such as remote computer 49. These logical connections are achieved by a communication device coupled to or a part of the computing device 12 (as the local computer). Implementations are not limited to a particular type of communications device. The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 4 include a local-area network (LAN) 51 and a wide-area network (WAN) 52. Such networking environments are commonplace in offices, enterprise-wide computer networks, intranets and the Internet.

When used in a LAN-networking environment, the computing device 12 is connected to the local area network 51 through a network interface or adapter 53, which is one type of communications device. When used in a WAN-networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

FIG. 5 illustrates at least a portion of the other program modules 37 (see FIG. 4). As explained above with reference to FIG. 4, the other program modules 37 are stored on the hard disk drive 27, magnetic disk 29, optical disk 31, ROM 24, or RAM 25. Thus, the other program modules 37 are stored on a memory of or accessible by the computing device 268 (see FIG. 3). Turning to FIG. 5, as mentioned above, the other program modules 37 may include the image analysis module 320, the positioning module 330, and the stimulus module 340.

When executed by one or more processors (e.g., the processing unit 21), the image analysis module 320 analyzes the right and left imaging signals (received from the right and left imaging devices 204 and 206, respectively) to identify the positions of the landmarks on the retinas 108 of the right and left eyes 104 and 106.

When executed by one or more processors (e.g., the processing unit 21), the positioning module 330 uses the positions of the landmarks on the retinas 108 of the right and left eyes 104 and 106 (determined by execution of the image analysis module 320) to generate the right and left positioning signals (described above). The positioning module 330 may also instruct the right adjustment mechanism 294, the left adjustment mechanism 296, the right adjustment mechanism 304, and the left adjustment mechanism 306 how to position the mirrors 224, 226, 234, and 236, respectively.

In embodiments in which the right and left arm assemblies 244 and 246 of the device 200 are positioned robotically as opposed to manually, the positioning module 330 may optionally be separated into two modules: (1) a first module including instructions for positioning the stimulus within the right visual display 214 and/or instructions for positioning the stimulus within the left visual display 216; and (2) a second module including instructions for positioning the right and left arm assemblies 244 and 246 and the positionable components thereof.

When executed by one or more processors (e.g., the processing unit 21), the stimulus module 340 provides the right and left stimulus signals to the right and left displays 214 and 216, respectively.

The device 200 may be used to measure an angle of a strabismus, both in patients who have a constant angle (such as concomitant esotropia) or an angle that changes over time (such as incomitant esotropia, intermittent tropias, and the like). The device 200 may be used to measure how the angle of the strabismus changes as a function of stimulus parameters such as the three dimensional location of a fixation target relative to the head. The device 200 may also be used to measure changes in eye position, such as vergence eye posture, that result from specific visual stimulation (for example a change in the vergence demand of the stimulus) or instructions given to the patient (such as instructions to look at a particular object or element within a three-dimensional display). As mentioned above, the device 200 may include ophthalmic lenses "L1" and "L2" positioned in the optical paths of the right and left eyes 104 and 106, respectively. The lenses "L1" and "L2" may be implemented using spherical lenses. By interpositioning spherical lenses between the right and left eyes 104 and 106 and the right and left visual displays 214 and 216, respectively, the operator may measure a specific visual response of clinical importance, the accommodation-convergence to accommodation ("AC/A") ratio, for each of the right and left eyes 104 and 106. The AC/A ratio is an amount by which the eyes converge in response to a change in the accommodation of the eye's lens or the accommodative demand of a visual display. Further, the operator may use the system to measure the AC/A ratio for only one of the patient's eyes by interpositioning a spherical lens into the visual path of only the right eye 104 or the left eye 106.

The device 200 may be used to an aid in deciding whether to proceed with a strabismus surgery, and which procedure or magnitude of surgical correction to employ. Because the device 200 may be configured to deliver highly controlled binocular stimuli, the placement of which can be made contingent on the current position of the right and left eyes 104 and 106, visual displays can be presented to the patient 100 to measure the timing and magnitude of changes in eye position that occur in response to the presentation of specific fixation targets or patterned images that contain binocular disparities. These displays can be updated dynamically to take into account changes in the positions of the right and left eyes 104 and 106. For example, the device 200 can be used to measure elicited vergence responses to a stimulus with "clamped" disparity, meaning a stimulus that is adjusted dynamically to take changes in vergence eye posture into account, thereby causing the stimulus to have a constant retinal disparity.

Also, changes in binocular disparity are known to elicit compensatory changes in vergence eye posture in the normal visual system. See Busettini C, Fitzgibbon E J, Miles F A., Short-latency disparity vergence in humans, *J Neurophysiol.* 2001 March; 85(3):1129-52. Therefore, operator-controlled changes in the binocular disparity of the stimulus can be used to assess vergence response (e.g., by measuring angular velocities of the two right and left eyes 104 and 106 elicited by a change in stimulus disparity as a function of magnitude and direction of change in stimulus disparity, and/or as a function of other static or dynamically changing stimulus factors, such as stimulus size, position within the visual field, luminance, contrast, pattern and spatial frequency content, translational velocity, and/or starting disparity). Except for disparity, which is inherently binocular, these stimulus factors may be the same in both eyes, or different in one eye and the other.

Also, each of the right and left eyes 104 and 106 initiate consensual ocular following movements in response to stimuli that translate similarly in the two eyes, and this elicited response is known to depend on the disparity of the stimulus. See Masson G S, Busettini C, Yang D S, Miles F A., Short-latency ocular following in humans: sensitivity to binocular disparity, *Vision Res.* 2001; 41(25-26):3371-87. The device 200 may be used to measure the magnitude of the consensual ocular following response as a function of static or dynamically changing stimulus factors such as stimulus size, position within the visual field, luminance, contrast, pattern and spatial frequency content, translational velocity, and/or the binocular disparity of the stimulus. Except for disparity, which is inherently binocular, these stimulus factors may be the same in both eyes, or different in one eye and the other.

The device 200 may be used to measure depth of suppression and treatment of suppression. Depth of suppression refers to an amount by which an amblyopic eye is inhibited from providing neural signals to the visual cortex.

Suppression is believed to occur primarily at two sites within the visual pathway in the brain: the LGN and V1. Suppression can occur when the nonamblyopic eye is occluded, in which case it persistently degrades vision when using the amblyopic eye alone. Suppression of the amblyopic eye is typically much stronger when both eyes are open. The device 200 can be used to measure the depth of suppression, which is a clinically important diagnostic marker of binocular function. Current computer-based methods of measuring suppression can be implemented using the device. For example, the methods described in the following publications, each of which is incorporated herein by reference in its entirety, may be implemented using the device 200: Ding J, Sperling G., A gain-control theory of binocular combination, *Proc Natl Acad Sci USA.* 2006 Jan. 24; 103(4):1141-6. Epub 2006 Jan. 12; Huang C B, Zhou J, Lu Z L, Feng L, Zhou Y., Binocular combination in anisometropic amblyopia, *J Vis.* 2009 Mar. 24; 9(3):17.1-16; and Black J M, Thompson B, Maehara G, Hess R F., A compact clinical instrument for quantifying suppression, *Optom Vis Sci.* 2011 February; 88(2):E334-43.

The device 200 can also be used to deliver treatments for suppression, such as the treatment described in Hess R F, Mansouri B, Thompson B., A binocular approach to treating amblyopia: antisuppression therapy, *Optom Vis Sci.* 2010 September; 87(9):697-704, which is incorporated herein by reference in its entirety. The methods of Hess et al. that measure and treat suppression operate through the presentation, to the patient 100, of stimuli that have greater luminance or contrast in the amblyopic eye than in the nonamblyopic eye. It is believed that these treatments may be made more effective by controlling the position of the binocular stimulus on the retinas with greater accuracy and precision, which could be provided by using the device 200 to deliver the stimuli.

The device 200 can also be used to develop and test new methods for measuring suppression, including the extent to which the suppression depends on such factors as stimulus size, position within the visual field, luminance, contrast, pattern and spatial frequency content, translational velocity, and/or starting disparity. Except for disparity, which is inherently binocular, these stimulus factors may be the same in both eyes, or different in one eye and the other. The device 200 can also be used to develop and test new methods for treating suppression, including but not limited to methods wherein stimulus contrast is made greater or less in the amblyopic eye relative to the nonamblyopic eye during binocular binocular training procedures. The differential between the eyes in the contrast of the stimulus could be constant across a parameter that characterizes the stimulus, or it could vary: for example, contrast could be selectively reduced in the nonamblyopic eye only at high spatial frequencies. The overall contrast difference between the eyes could be increased or decreased over time during the course of the anti-suppression treatment. It is believed that any such measurement or treatment may be made more effective through active control of binocular stimulus position on the retinas, which may be provided by the device 200.

Increasing the signal strength from the amblyopic eye relative to the nonamblyopic eye is a general principle of treatment for binocular vision, because it is believed to be necessary for training the brain how to interpret binocular stimuli. To achieve this relative strengthening, most currently performed procedures for treating amblyopic suppression employ stimuli that have greater contrast in the amblyopic eye. Another method of treating suppression is "reverse patching." In this treatment, the patient wears a patch over the amblyopic eye, instead of the nonamblyopic eye. The principle behind this treatment is that when the brain is deprived of its usual input from the amblyopic eye, it may turn up the gain on outputs from the amblyopic eye in order to restore their strength to the level to which it has become accustomed over the life of the patient. This increased gain is believed by some practitioners to last long enough after the patch is removed to be exploited for treatment. The method of reverse patching is described in John R. Griffin MOpt OD MSEd and J. David Grisham OD MS FAAO, Binocular Anomalies: Diagnosis and Vision, Butterworth-Heinemann; 4 edition (Jun. 15, 2002), which is incorporated herein by reference in its entirety. The device 200 may be used to deliver stimuli that have greater contrast in the nonamblyopic eye (instead of the amblyopic eye), to target gain control mechanisms, thereby effecting an increase in signal strength from the amblyopic eye at the site of binocular combination in visual cortex.

The device 200 may be used to locate visual deficits in each eye, and consequent functional deficits with binocular vision, in patients with age-related macular degeneration ("AMD"), glaucoma, diabetic retinopathy, retinal detachment, and other retinal disease. In particular, the device 200 could be configured to provide precise spatial mapping in retinal coordinates of scotomas resulting from ocular disease. Existing devices (such as the Centervue "Maia" system, and the Nikek "MP-1" system) can perform these functions, but only for one eye at a time. Therefore, existing devices cannot test both eyes simultaneously. In particular, existing devices cannot measure the patient's ability to detect binocularly presented visual targets. Because the device 200 may include a separate component system for each eye, monocular testing of both eyes separately may be performed without moving the device from one eye to the other, and without moving the patient's head.

The device 200 may be configured to provide precise perimetry (retinotopic mapping of visual scotomas) in patients with stroke or other brain injury.

Patients with strabismus often position their eye so that some part of the retina 108 other than the fovea 114 receives the image of a fixated object. Eccentric fixation refers to the habit of using some specific part of the retina 108, other than the fovea 114, to fixate objects. This effect is a monocular phenomenon. Eccentric fixation can be measured in each eye using the device 200 without moving the device from one eye to the other, and without moving the patient's head The device 200 may be configured to determine visual fields (perimetry) in persons with nystagmus.

The device 200 may be configured to measure low vision. Another population of patients that may be served by the device 200 is the population of patients that have low vision. Many people with low vision have difficulty fixating, or have eccentric fixation. It is believed that using the device 200 may be used to provide better perimetry for this population compared to prior art methods by tying the visual field to an objective map of the retina 108 rather than determining the visual field relative to a mark the patient was asked to fixate. Low vision may be measured in each eye using the device 200 without moving the device from one eye to the other, and without moving the patient's head.

Embodiments of the device 200 may be constructed and configured to automate many traditional procedures used in the assessment and treatment of binocular anomalies and amblyopia. By way of non-limiting examples, the following procedures may be automated using the device 200:

1. measurement of angle of strabismus;
2. measurement of oculomotor response to change in disparity (challenge);
3. measurement of maximum perceptual response (stereopsis) for optimally placed binocular stimuli;
4. treatment to establish fusion before and/or after strabismus surgery;
5. treatment of amblyopia and strabismus using perceptual learning paradigm: practice controlling vergence eye posture;
6. treatment of amblyopia and strabismus using perceptual learning paradigm: practice perceiving depth within visual stimuli that contain binocular disparity;
7. classic vision therapy treatments for amblyopia that require establishing binocularity and fusion through the use of dichoptic displays;
8. measurement of binocular retinal correspondence, especially the detection and characterization of anomalous retinal correspondence (ARC);
9. temporary incapacitation of nonfoveal retina in an amblyopic eye, by means of bright bleaching light: this procedure is believed to increase the likelihood that the patient will fixate using the anatomical fovea of the amblyopic eye; and 10. creation of visual afterimages at known retinal locations in the amblyopic and/or nonamblyopic eye: the apparent location of the afterimage relative to fixation, or relative to visible objects displayed at known locations on the retina of the same eye or other eye being a method used during measurement and treatment of anomalous retinal correspondence (ARC).

It is often useful for clinical or research purposes to keep the same image on one part of the retina 108 for an extended period of time. This is called a stabilized retinal image. Stabilized retinal images fade perceptually over the course of a few seconds, and the rate of fading provides a measure of the time constants that characterize adaptation processes in the retinal 108 and later stages of visual processing in the nervous system. Embodiments of the device 200 may be constructed and configured to stabilize an image on the retina 108.

Eye movements are thought to contribute importantly to perception, but the exact nature of their contribution is unknown, owing to the current difficulty in measuring small eye movements such as microsaccades, drift, and tremor. Embodiments of the device 200 may be constructed and configured to monitor very small (e.g., less than about 5 arcmin) and/or very rapid eye (power at high temporal frequency, e.g., at greater than about 4 Hz) movements.

Embodiments of the device 200 may be constructed and configured to measure visual attention to locations in 3D space. For example, such embodiments may be used to monitor attention within 3D scenes, as indicated by the fixation positions of the eyes (version and vergence eye postures, taken together).

Embodiments of the device 200 may be constructed and configured to quantify how well a patient follows instructions to fixate a specified visual target. For example, such embodiments may monitor whether a person maintains fixation on a visual target according to instructions, and the pattern of deviation from accurate fixation.

Embodiments of the device 200 may be constructed and configured to measure binocular responses to change in accommodative demand. For example, the device 200 may include automatic mechanism to control the focus (e.g., an autofocus mechanism) of the displayed images on the retinas. In such embodiments, the device 200 may be used to measure binocular motor and perceptual responses, and accommodative responses, to stimuli that are presented with specific accommodative demand (e.g., out of focus), or that change in accommodative demand over time. One non-limiting example is the measurement of the ACA ratio (amount of accommodation-driven convergence per unit accommodative demand).

Embodiments of the device 200 may be constructed and configured to measure accommodative response to change in binocular disparity. For example, the device 200 may include automatic mechanism to control the focus (e.g., an autofocus mechanism) of the displayed images on the retinas. In such embodiments, the device 200 may be used to measure binocular motor and perceptual responses, and accommodative responses, to stimuli that are presented with specific vergence demand (i.e. binocular disparity), or that change in vergence demand over time. One non-limiting example is the measurement of the CAC ratio (amount of convergence-driven accommodation per unit change in vergence demand).

Embodiments of the device 200 may be constructed and configured to measure binocular visual responses, and to present binocular stimuli to known retinal locations, in non-verbal humans, such as infants or persons who are unable to understand speech after trauma.

Embodiments of the device 200 may be constructed and configured to measure binocular visual responses, and to present binocular stimuli to known retinal locations, in non-human primates and other animals.

The instructions of each of the modules 320, 330, and 340 may be stored on one or more non-transitory computer-readable media. The instructions of each of the modules are executable by one or more processors (e.g., the processing unit 21) and when executed perform the functions described above.

The device 200 is configured to provide simultaneous binocular stimulation at known retinal locations (e.g., locations relative to landmarks on the retina such as the fovea 114, the optic nerve head 116, and the like) in a person (e.g., the patient 100) who is not able to achieve reliable binocular fixation. Such a person may have a history of strabismus. When a person unable to achieve reliable binocular fixation is asked to look at a visible fixation target, the person typically achieves fixation by foveating the binocular target with one eye (e.g., the left eye 106) but not the other (e.g., the right eye 104). The device 200 allows a clinician or scientist to provide direct and precise binocular stimulation, rather than the more diffuse and spatially uncertain stimulation currently possible, using visual stimuli (e.g., patterns) provided at corresponding locations on the retinas of both the right and left eyes 104 and 106 simultaneously.

The device 200 may improves upon prior art methods, such as those performed by haploscopes, amblyoscopes, and synoptophores, by (1) allowing the display of spatiotemporal patterns that match known receptive field properties of binocular neurons in the visual cortex (such as drifting Gabor patterns) and (2) allowing precise placement of these displays at corresponding locations on the retinas of the right and left eyes 104 and 106. The device 200 may be configured to provide binocularly correlated input to the visual system appropriate for visual neurons in the brain's visual cortex. Conventional technologies are unable to provide such input.

Without being limited by theory, it is believed learning by neurons is nonlinear. For this reason, it is believed that one second of high contrast optimal stimulation provided in a 60 second period may cause a greater change in the way in which a neuron responds than 60 seconds of continuous stimulation having 1/60 the contrast, even though the same neurons will respond to both of these stimuli.

Support for the belief that learning by neurons is nonlinear is found in other known effects in the visual system. The McCollough effect, for example, is a long-lasting adaptation after effect caused by exposure to high contrast stimuli but not low contrast stimuli. This effect is explained in Siegel, S. and Allan, L. G., Pairings in Learning and Perception: Pavlovian Conditioning and Contingent Aftereffects, Psychology of Learning and Motivation, Academic Press, Vol. 28, 127-160 (1992), which is incorporated herein by reference in its entirety.

The device 200 may expose different classes of neurons to optimal stimulation patterns, at high contrast, for short amounts of time at different times for different classes. This can be done simultaneously at many locations within the visual field because the visual neurons responsible for early visual processing (which are the sites of binocular combination) respond to stimuli at specific locations on the retinas 108. Visual stimuli may be swept across many orientations and spatial frequencies to train some or all of the classes of visual neurons. A subset of orientations or spatial frequencies may be used to determine whether suppression is eliminated selectively for the subset.

Without being limited by theory, it is believed that binocular vision therapies and methods of treating suppression in particular, are effective because they use stimuli to which binocular visual neurons in the brain respond. By targeting specific classes of neurons one at a time, using high contrast stimuli at specific spatial frequencies, orientations, and disparities, neurons in each class might reasonably be expected to change its responses to the stimuli more rapidly than the neurons would in response to the diffuse and spatially uncertain stimulation provided by prior art scattershot approaches.

The device 200 may be used to provide binocular visual stimulation to treat patients with residual strabismus after orthoptic surgery. The device 200 may be used before surgery to help patients develop binocular vision, which could help improve surgical outcomes, or in some cases make the surgery unnecessary. The visual stimulation may be matched to known properties of the neurons in the brain's visual cortex, so the device 200 can be used for experiments to determine whether perceptual learning can be used as a therapy to improve binocular function in strabismic and amblyopic patients. Improvement in binocular function may include: reduction in the strength (depth) of suppression, increased accuracy and precision of binocular fixation (eye alignment), greater change in vergence eye posture in response to unit change in stimulus disparity, increase in the ability to perceive depth from binocular disparities, correction of anomalous binocular correspondence, inability to fuse, diplopia, visual confusion, or inability to use binocular disparity as a cue for visual segmentation of images into parts that correspond to discrete objects.

Alternate Embodiment

In an alternate embodiment, the right and/or left imaging devices 284 and 286 are implemented using one or more eye imaging devices (as opposed to retina imaging devices), such as one or more eye trackers. Instead of imaging the retina 108, an eye tracker images at least one of the right and left eyes 104 and 106 and determines the position of the eye(s) relative to the appropriate display device or devices. By way of a non-limiting example, an eye tracker may include one or more camera and software executed by a computing device (e.g., the computing device 268). When executed the software may perform one or more methods of monitoring eye position (eye tracking). For ease of illustration, these methods will be described with respect to monitoring the position of the right eye 104. However, as is appreciated by those of ordinary skill in the art, substantially similar methods may be used to monitor the position of the left eye 106.

An exemplary method of eye tracking includes using a video camera to monitor the structures at the front of the right eye 104 that are visible in an image of the front of the right eye 104. In such an embodiment, video images are used to calculate eye position based on one or more of the following structures: pupil, pupil margins, iris, or limbus (the iris-sclera boundary). By way of another non-limiting example, eye tracking may be implemented using Purkinje image tracking. Alternatively, eye tracking may be implemented using electrooculography ("EOG"). By way of another non-limiting example, eye tracking may be implemented using the measurement of differential light reflection from opposite sides of the right eye 104 as is typically done using infrared emitters and a set of detectors pointed at the limbus.

Depending upon the implementation details, eye tracking may determine the position of the right eye 104 in two-dimensions (equivalent to elevation and azimuth), three-dimensions (equivalent to elevation, azimuth, and torsion; e.g., roll, pitch, and yaw), six-dimensions, which includes the translational position of the entire eye (equivalent to elevation, azimuth, torsion, x, y, and z, where [x,y,z] describes the location of the center of the right eye 104 or some other part of the eye). Implementations in which eye position include torsion may more accurately determine an amount by which the eye is rotated about the visual axis.

When eye tracking is used, a correspondence between eye position, and retinal position of the visual stimulation may be inferred. To stimulate a specific location on the retina 108 using the right visual display 214 and a measurement of eye position, one may use a model that relates the location of the stimulus relative to the right eye 104 to the position of the image of stimulus (which can be conceived of as a point in space) on the retina 108. Projection through the optical center (or nodal point) of the right eye 104 is one such model. The optical center of the human eye is typically about 7 mm behind the front of the cornea and about 17 mm in front of the fovea 114, on the optical axis of the eye. See A. Gullstrand, in Helmholtz's Physiological Optics, *Optical Society of America*, New York, 1924, Appendix, pp. 350-358. The right eye 104 itself can be modeled as a sphere or ellipsoid. However, the right eye 104 may not actually be a sphere; the right eye 104 can be elongated in persons with myopia, and shortened in persons with hyperopia. Therefore, the location on the retina 108 at which the image of an external object falls can be computed as a pair of numbers that describe the location of the image relative to the fovea 114. The pair of numbers can describe either deviation from the fovea 114 in units of visual angle (such as degrees of elevation and degrees of azimuth) or units of spatial extent (such as millimeters up or down in the vertical direction and millimeters left or right in the horizontal direction) relative to the fovea 114 and horizontal meridian of the right eye 104. This computation can be made from the angle formed by a point on the object in space, the optical center, and the visual axis of the right eye 104 (the visual axis is the line that contains the fovea 114 and the optical center), with the optical center at the vertex of the angle, together with the rotational orientation (about the visual axis) of the plane that contains this angle. The estimated retinal location of the image of the point, when defined by a pair of visual angles, is equal in magnitude and opposite in sign to the elevation and azimuth of the point relative to the right eye 104. When defined in units of spatial extent, it is the intersection of the retina 108 with the line that contains the point and optical center of the right eye 104, where the location of the retina 108 must be inferred from an estimate of the shape of the globe of the right eye 104 (using normative data or direct measurement).

To stimulate a specific retinal location using a visual display and a measurement of eye position (as collected by the eye tracker), one also needs to estimate the retinal position of the fovea 114. The location of the fovea 114 within the right eye 104, relative to the estimate of eye position determined by monitoring the right eye 104 (but is not based on an image that includes the fovea 114), may be inferred using one or more of the following three exemplary methods:

(a) the location of the fovea 114 within the right eye 104 may be inferred based on normative data (average of data collected from many people);

(b) the location of the fovea 114 within the right eye 104 may be established for a given person using a calibration procedure that may build a look-up table or define a function that describes the correspondence; and (c) the location of the fovea 114 within the right eye 104 may be determined based on a subjective procedure that depends intrinsically on the patient following instructions that result in a known eye position, such as instructing the patient where to look.

In the method (a), a new patient's foveal position relative to the right visual display 214 at any given time may be inferred from the physical direction of, and the right eye's torsion about, the visual axis, as estimated from monitored eye position (using the eye tracker).

The method (b) may be more reliable than the methods (a) and (c) because the method (b) is specific to the individual and thus not subject to error from individual variation in the shape of the structures of the right eye 104 (unlike the method (a)), and is not subject to systematic errors of fixation (unlike the method (c)). The calibration step in the method (b) may be accomplished using a retinal imaging mechanism (such as the right imaging device 204), and the eye tracker. By way of a non-limiting example, the eye tracker may be implemented using one or more video cameras. As the eyes are moved over time, either by instructing the patient 100 to move his/her eyes, or waiting for the eyes to move spontaneously, the image of the retina 108 changes and so does the measure of eye position from the eye tracker. The device 200 may be configured to make direct determinations of the locations in space at which objects can be placed to stimulate the imaged parts of the retina 108, so the same locations in space can be assumed to stimulate the same portions of retina 108 again when the right eye 104 is once again in the same positions as determined using the eye tracker.

Sampling of data triplets (eye position according to eye tracker, location in space of the object, and location of the image on the retina 108) may be captured at any sampling rate, and for any length of time, but in practice it may take only a few minutes to accumulate enough data to use monitored eye position rather than retinal imaging to know where in space a visual stimulus must be placed to position its image at a desired location on the retina 108. A lookup table could be built from the data triplets, and used by means of interpolation and extrapolation to determine such a location in space, or else the positions in space could be determined from the parameters of a function (such as a multivariate polynomial) fitted to the accumulated data.

In the method (c), a new patient's retinal image position relative to the right visual display 214 may be inferred from a lookup table created by asking the patient 100 to fixate on a sequence of targets on the display using the right eye 104. Then, the process may be repeated for the left eye 106 (as is common practice for the calibration step required to use most eye trackers).

As mentioned above, the methods described above with respect to the right eye 104 may be used or adapted for use with the left eye 106.

Optionally, the right imaging device 204 may perform both retinal imaging and eye imaging (e.g., using an eye tracker) and the left imaging device 206 may perform both retinal imaging and eye imaging (e.g., using an eye tracker). Alternatively, the device 200 may include a right eye tracker (not shown) that is separate from the right imaging device 204 and a left eye tracker (not shown) that is separate from the left imaging device 206. In such embodiments, the right and left imaging devices 204 and 206 may be configured to perform only retinal imaging.

In embodiments of the device 200 configured to perform both retinal imaging and eye imaging, imaging the retina 108 during eye tracking may be used to improve the accuracy and precision of the eye tracking because an eye tracker can be objectively calibrated using the retinal locations of the images created using objects that have known locations in space. For ease of illustration, the following exemplary method will be described with respect to the right eye 104. However, a substantially similar method may be used with respect to the left eye 106. For example, the patient 100 may be shown two small lights "A" and "B" (not shown) separated by a visual angle "M" (e.g., measured in degrees), and asked to fixate on each of the lights in turn. During fixation on the light "A," the locations of the images of the lights "A" and "B" on the retina 108 (relative to any visible landmark) may be recorded (e.g., as retinal locations "A1" and "B1," respectively). Also, the location of the right eye 104 determined using eye tracking (e.g., pupil location) may be recorded. Then, the patient 100 may be instructed to fixate light "B." The retinal locations of the images of lights "A" and "B" may be recorded e.g., as retinal locations "A2" and "B2," respectively). Also, the location of the right eye 104 determined using eye tracking (e.g., pupil location) may be recorded. Next, the magnitude of the actual rotation angle of the right eye 104 during the fixation change from the light "A" to the light "B" can be computed. For example, it could be computed as the visual angle "M" multiplied by a scalar "F." The scalar "F" is equal to the distance between the retinal locations "B1" and "B2" divided by the distance between retinal locations "A1" and "B1." Similarly, the retinal locations "A1," "B1," "A2," and "B2" may be used to determine the true direction of the eye movement. Similarly, one could determine separately for fixation on the lights "A" and "B" what the accuracy and precision of the fixation is, by comparing the retinal location "A1" to the location of the fovea 114, and the retinal location "B2" to the location of the fovea, respectively, and using this measurement to interpret the location of the right eye 104 determined using eye tracking. During the calibration of a traditional eye tracker, one must make an assumption about the accuracy of fixation (e.g., on points such as the lights "A" and "B") to interpret the measure related to eye position as an actual eye position. Using the new method described above, actual eye position during fixation can be measured. These measurements can then be used to accurately determine fixation from the measures of eye position even without continued monitoring of retinal image position.

Another alternate embodiment of the device 200 may be constructed using an external eye position monitor or eye tracker (not shown) and a single display device (not shown). In such an embodiment, the patient views the single display device instead of the two right and left visual display devices 214 and 216, and separation of the images of the left and right eyes 104 and 106 may be effected using one or more of the following components:

(1) anaglyph glasses and a colored display;
(2) polarized glasses and polarized display pixels;
(3) shutter goggles and a field-sequential display;
(4) a lenticular cover on the display; and
(5) a Brewster stereoscope that makes a different half of the display visible to each eye.

The eye position monitored by the external eye position monitor could be determined using any of the aforementioned methods (e.g., the method (a), the method (b), and the method (c)).

In some embodiments, the eye tracker may be implemented using a single video camera device positioned to image the front of both of the right and left eyes 104 and 106 at the same time. In such embodiments, the single video camera device may replace the right and left imaging devices 204 and 206 or be included in addition to the right and left imaging devices. The single video camera device may be separate from the single display device (not shown) described above. Alternatively, the single video camera device may be built into the single display device (as is often the case for a laptop computer or tablet-style computer). In embodiments including the right and left visual display devices 214 and 216, the single video camera device may be separate from the right and left visual display devices 214 and 216. Alternatively, the single video camera device may be built into one of the right and left visual display devices 214 and 216.

Optionally, the single camera device (not shown) may be modified using prisms and/or focusing lenses so that the image of each of the right and left eyes 104 and 106 occupies a greater part of the camera's field of view, and the camera does not image the bridge of the nose. The prisms and/or focusing lenses may increase the precision of external eye position measurements by increasing the size of the image of each of the right and left eyes 104 and 106.

Eye tracking (whether implemented using a single device or separate right and left devices) may be used to extend accurately localized visual stimulation to retinal locations outside the view of the right and left (retina) imaging devices 204 and 206. In other words, eye tracking may be used to extend the size of the visual field that can be stimulated at known retinal locations, by using eye position (obtained from eye tracking) to determine a point in space that will be imaged at a desired location on the retina 108, when that part of the retina is outside the field of view of the right and left (retina) imaging devices 204 and 206.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A system for use with a patient having a brain, a left eye with a left retina, and a right eye with a right retina, the system comprising:

at least one retina imaging device positionable to capture an image of the patient's right retina and an image of the patient's left retina;

at least one visual display device positionable to provide right visual stimulation to the patient's right retina in response to a right positioning signal, and left visual stimulation to the patient's left retina in response to a left positioning signal;

a computing device configured to execute instructions that when executed instruct the computing device to (a) receive the image of the patient's right retina and the image of the patient's left retina from the at least one retina imaging device, (b) identify a location on the patient's right retina based at least in part on the image of patient's right retina, (c) identify a corresponding location on the patient's left retina based at least in part on the image of patient's left retina, a first image positioned at the location identified on the patient's right retina and a second image simultaneously positioned at the corresponding location on the patient's left retina being fusable by the patient's brain into a single fused image, (d) transmit the right positioning signal to the at least one visual display device indicating where the right visual stimulation is to be displayed by the at least one visual display device, the right visual stimulation being positioned at the location identified on the patient's right retina when displayed by the at least one visual display device, and (e) transmit the left positioning signal to the at least one visual display device indicating where the left visual stimulation is to be displayed by the at least one visual display device, the left visual stimulation being positioned at the corresponding location identified on the patient's left retina when displayed by the at least one visual display device.

2. The system of claim 1, wherein the instructions further instruct the computing device to identify a landmark in the image of the patient's right retina and a corresponding landmark in the image of the patient's left retina, the location identified on the patient's right retina being identified based at least in part on the location of the landmark, and the corresponding location identified on the patient's left retina being identified based at least in part on the location of the corresponding landmark.

3. The system of claim 2 for use with the patient's right eye comprising an optic disc and a pattern of blood vessels and the patient's left eye comprising an optic disc and a pattern of blood vessels, wherein the at least one retina imaging device comprises a video camera, the landmark is the optic disc of the patient's right eye or a specific location identified in relation to the pattern of blood vessels of the patient's right eye, and the corresponding landmark is the optic disc of the patient's left eye or a specific location identified in relation to the pattern of blood vessels of the patient's left eye.

4. The system of claim 1, wherein the at least one retina imaging device implements scanning laser ophthalmoscopy ("SLO").

5. The system of claim 1, wherein the right and left visual stimulation each comprise a Gabor pattern, or a series of patterns.

6. The system of claim 1, wherein the at least one retina imaging device comprises a right retina imaging device and a left retina imaging device, the right retina imaging device being positionable to capture the image of the patient's right retina, the left retina imaging device being positionable to capture the image of the patient's left retina;

the at least one visual display device comprises a right visual display device and a left visual display device, the right visual display device being positionable to provide the right visual stimulation to the patient's right retina in response to the right positioning signal, and the left visual display device being positionable to provide the left visual stimulation to the patient's left retina in response to the left positioning signal; and the system further comprises:

a right arm assembly, the right retina imaging device and the right visual display device being mounted on the right arm assembly, the right arm assembly being movable relative to the patient to position the right retina imaging device and the right visual display device relative to the patient's right retina; and a left arm assembly, the left retina imaging device and the left visual display device being mounted on the left arm assembly, the left arm assembly being movable relative to the patient to position the left retina imaging device and the left visual display device relative to the patient's left retina.

7. The system of claim 6, wherein the right retina imaging device generates a right scanning signal, the left retina imaging device generates a left scanning signal, and the system further comprises:

a right mirror mounted on the right arm assembly and positioned to receive the right visual stimulation, reflect the right visual stimulation onto the patient's right retina, receive the right scanning signal from the right retina imaging device, and reflect the right scanning signal onto the patient's right retina, the patient's right retina reflecting the right scanning signal back toward the right mirror as a returning right scanning signal, the right mirror being positioned to reflect the returning right scanning signal back toward the right retina imaging device;

a half-silvered right mirror mounted on the right arm assembly and positioned to receive the right stimulation signal from the right visual display device, reflect the right stimulation signal onto the right mirror, and allow both the right scanning signal from the right retina imaging device and the returning right scanning signal to pass therethrough;

a left mirror mounted on the left arm assembly and positioned to receive the left visual stimulation, reflect the left visual stimulation onto the patient's left retina, receive the left scanning signal from the left retina imaging device, and reflect the left scanning signal onto the patient's left retina, the patient's left retina reflecting the left scanning signal back toward the left mirror as a returning left scanning signal, the left mirror being positioned to reflect the returning left scanning signal back toward the left retina imaging device; and a half-silvered left mirror mounted on the left arm assembly and positioned to receive the left stimulation signal from the left visual display device, reflect the left stimulation signal onto the left mirror, and allow both the left scanning signal from the left retina imaging device and the returning left scanning signal to pass therethrough.

8. The system of claim 1, further comprising:

a right lens positionable adjacent the patient's right eye; and a left lens positionable adjacent the patient's left eye.

9. The system of claim 8, wherein the right and left lenses are each spherical lenses.

10. A system for use with a patient having a brain, a left eye with a left retina, and a right eye with a right retina, the system comprising:

at least one eye imaging device positionable to capture an image of the patient's right eye and an image of the patient's left eye;

at least one visual display device positionable to provide right visual stimulation to the patient's right retina in response to a right positioning signal, and left visual stimulation to the patient's left retina in response to a left positioning signal;

a computing device configured to execute instructions that when executed instruct the computing device to (a) receive the image of the patient's right eye and the image of the patient's left eye from the at least one eye imaging device, (b) determine a position of the patient's right eye, (c) identify a right stimulation location for the patient's right eye based at least in part on the position of the patient's right eye, (d) determine a position of the patient's left eye, (e) identify a left stimulation location for the patient's left eye based at least in part on the position of the patient's left eye, a first image positioned at the right stimulation location and a second image simultaneously positioned at the left stimulation location being fusable by the patient's brain into a single fused image, (f) transmit the right positioning signal to the at least one visual display device indicating where the right visual stimulation is to be displayed by the at least one visual display device, the right visual stimulation being positioned at the right stimulation location when displayed by the at least one visual display device, and (g) transmit the left positioning signal to the at least one visual display device indicating where the left visual stimulation is to be displayed by the at least one visual display device, the left visual stimulation being positioned at the left stimulation location when displayed by the at least one visual display device.

11. The system of claim 10, wherein the at least one eye imaging device comprises one or more video cameras.

12. The system of claim 10, further comprising at least one retina imaging device configured to capture images of the patient's right and left retinas, wherein the instructions further instruct the computing device to (a) identify locations on the patient's right retina based on the images of the patient's right retina and correlate the locations identified with positions of the patient's right eye, and (b) identify locations on the patient's left retina based on the images of the patient's left retina and correlate the locations identified with positions of the patient's left eye.

13. The system of claim 10, wherein the right and left visual stimulation each comprise a Gabor pattern, or a series of patterns.

14. The system of claim 10, wherein the at least one eye imaging device comprises a right eye imaging device and a left eye imaging device, the right eye imaging device being positionable to capture the image of the patient's right eye, the left eye imaging device being positionable to capture the image of the patient's left eye.

15. The system of claim 10, wherein the at least one visual display device comprise a right visual display device and a left visual display device, the right visual display device being positionable to provide the right visual stimulation to the patient's right retina in response to the right positioning signal, and the left visual display device being positionable to provide the left visual stimulation to the patient's left retina in response to the left positioning signal.

16. The system of claim 10, wherein the at least one eye imaging device comprises a right eye imaging device and a left eye imaging device, the right eye imaging device being positionable to capture the image of the patient's right eye, the left eye imaging device being positionable to capture the image of the patient's left eye;

the at least one visual display device comprise a right visual display device and a left visual display device, the right visual display device being positionable to provide the right visual stimulation to the patient's right retina in response to the right positioning signal, and the left visual display device being positionable to provide the left visual stimulation to the patient's left retina in response to the left positioning signal; and the system further comprises:

a right arm assembly, the right eye imaging device and the right visual display device being mounted on the right arm assembly, the right arm assembly being movable relative to the patient to position the right eye imaging device and the right visual display device relative to the patient's right eye; and a left arm assembly, the left eye imaging device and the left visual display device being mounted on the left arm assembly, the left arm assembly being movable relative to the patient to position the left eye imaging device and the left visual display device relative to the patient's left eye.

17. A non-transistory computer readable storage medium for use with a right visual display device operable to display right visual stimulation, a left visual display device operable to display left visual stimulation, and a patient having a brain, a left eye with a left retina, and a right eye with a right retina, the one or more computer-readable media comprising instructions that when executed instruct one or more processors to perform a method comprising: receiving an image of the patient's right eye and an image of the patient's left eye; identifying a location on the patient's right retina based at least in part on the image of patient's right eye; identifying a corresponding location on the patient's left retina based at least in part on the image of patient's left eye, a first image positioned at the location identified on the patient's right retina and a second image simultaneously positioned at the corresponding location on the patient's left retina being fusable by the patient's brain into a single fused image; transmitting a right positioning signal to the right visual display device indicating where the right visual stimulation is to be displayed by the right visual display device, the right visual stimulation being positioned at the location identified on the patient's right retina when displayed by the right visual display device, and transmitting a left positioning signal to the left visual display device indicating where the left visual stimulation is to be displayed by the left visual display device, the left visual stimulation being positioned at the corresponding location identified on the patient's left retina when displayed by the left visual display device.

18. A non-transistory computer readable storage medium of claim 17 for use with a right positioning assembly and a left positioning assembly, the right visual display device being mounted to the right positioning assembly and the left visual display device being mounted to the left positioning assembly, wherein the method further comprises: transmitting a signal to the right positioning assembly instructing the right positioning assembly to position the right visual display device relative to the patient such that the right visual stimulation is positionable on the patient's right retina; and transmitting a signal to the left positioning assembly instructing the left positioning assembly to position the left visual display device relative to the patient such that the left visual stimulation is positionable on the patient's left retina.

19. A non-transistory computer readable storage medium of claim 18 for use a right imaging device mounted to the right positioning assembly and a left imaging device mounted to the left positioning assembly, the right imaging device being configured to capture the image of the patient's right eye and the left imaging device being configured to capture the image of the patient's left eye, wherein the method further comprises: transmitting a signal to the right positioning assembly instructing the right positioning assembly to position the right imaging device to capture the image of the patient's right eye; and transmitting a signal to the left positioning assembly instructing the left positioning assembly to position the left imaging device to capture the image of the patient's left eye.

20. A non-transistory computer readable storage medium of claim 17, wherein the image of the patient's right eye comprises an image of the patient's right retina and the image of the patient's left eye comprises an image of the patient's left retina.

21. A method for use with (a) a patient having a brain, a left eye with a left retina, and a right eye with a right retina, (b) a right visual display device operable to display right visual stimulation, (c) a left visual display device operable to display left visual stimulation, (d) at least one imaging device positionable to capture an image of the patient's right eye and an image of the patient's left eye, the method comprising:

receiving an image of the patient's right eye and an image of the patient's left eye from the at least one imaging device;

identifying a location on the patient's right retina based at least in part on the image of patient's right eye;

identifying a corresponding location on the patient's left retina based at least in part on the image of patient's left eye, a first image positioned at the location identified on the patient's right retina and a second image simultaneously positioned at the corresponding location on the patient's left retina being fusable by the patient's brain into a single fused image;

transmitting a right positioning signal to the right visual display device indicating where the right visual stimulation is to be displayed by the right visual display device, the right visual stimulation being positioned at the location identified on the patient's right retina when displayed by the right visual display device, and transmitting a left positioning signal to the left visual display device indicating where the left visual stimulation is to be displayed by the left visual display device, the left visual stimulation being positioned at the corresponding location identified on the patient's left retina when displayed by the left visual display device.

22. The method of claim 21 for use with a right positioning assembly and a left positioning assembly, the right visual display device being mounted to the right positioning assembly and the left visual display device being mounted to the left positioning assembly, wherein the method further comprises:

transmitting a signal to the right positioning assembly instructing the right positioning assembly to position the right visual display device relative to the patient such that the right visual stimulation is positionable on the patient's right retina; and transmitting a signal to the left positioning assembly instructing the left positioning assembly to position the left visual display device relative to the patient such that the left visual stimulation is positionable on the patient's left retina.

23. The method of claim 22 for use the at least one imaging device comprising a right imaging device mounted to the right positioning assembly and a left imaging device mounted to the left positioning assembly, the right imaging device being configured to capture the image of the patient's right eye and the left imaging device being configured to capture the image of the patient's left eye, wherein the method further comprises:

transmitting a signal to the right positioning assembly instructing the right positioning assembly to position the right imaging device to capture the image of the patient's right eye; and transmitting a signal to the left positioning assembly instructing the left positioning assembly to position the left imaging device to capture the image of the patient's left eye.

* * * * *